(12) United States Patent
Blaha

(10) Patent No.: US 7,637,907 B2
(45) Date of Patent: Dec. 29, 2009

(54) SYSTEM AND METHOD FOR RETURN ELECTRODE MONITORING

(75) Inventor: Derek M. Blaha, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 393 days.

(21) Appl. No.: 11/523,210

(22) Filed: Sep. 19, 2006

(65) Prior Publication Data

US 2008/0071263 A1    Mar. 20, 2008

(51) Int. Cl.
*A61B 18/16* (2006.01)
(52) U.S. Cl. .............................. 606/35; 606/32; 606/34
(58) Field of Classification Search ............. 606/34–35, 606/37–40
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,536,271 A | 1/1951 | Fransen et al. |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,380,445 A | 4/1968 | Frasier |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |

(Continued)

FOREIGN PATENT DOCUMENTS

CA    1219642    3/1987

(Continued)

OTHER PUBLICATIONS

International Search Report EP 07008207.8, dated Sep. 5, 2007.

(Continued)

*Primary Examiner*—Michael Peffley
*Assistant Examiner*—Amanda Scott

(57) ABSTRACT

A system for monitoring a plurality of return electrodes is disclosed. The system includes a plurality of return electrodes adhered to a patient and adapted to couple to an electrosurgical generator configured to generate an electrosurgical current. The system also includes a current monitor connected in series with each of the plurality of the return electrodes to measure a current signal passing therethrough and a processor coupled to each of the current monitors. The processor is configured to determine a desired current ratio and an actual current ratio for each of the plurality of the return electrodes as a function of the current passing through each of the plurality of the return electrodes. The processor is further configured to compare the desired current ratio and the actual current ratio.

12 Claims, 6 Drawing Sheets

U.S. PATENT DOCUMENTS

| | | |
|---|---|---|
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,534,306 A | 10/1970 | Watrous et al. |
| 3,543,760 A | 12/1970 | Bolduc |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,812,861 A | 5/1974 | Peters |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 3,987,796 A | 10/1976 | Gonser |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,067,342 A | 1/1978 | Burton |
| 4,074,719 A | 2/1978 | Semm |
| 4,092,985 A | 6/1978 | Kaufman |
| 4,092,986 A | 6/1978 | Schneiderman |
| 4,094,320 A | 6/1978 | Newton et al. |
| 4,102,341 A | 7/1978 | Ikuno et al. |
| 4,114,622 A | 9/1978 | Gonser |
| 4,114,623 A | 9/1978 | Meinke et al. |
| 4,117,846 A | 10/1978 | Williams |
| 4,121,590 A | 10/1978 | Gonser |
| 4,123,673 A | 10/1978 | Gonser |
| 4,126,137 A | 11/1978 | Archibald |
| 4,166,465 A | 9/1979 | Esty et al. |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,213,463 A | 7/1980 | Osenkarski |
| 4,231,372 A | 11/1980 | Newton |
| 4,232,676 A | 11/1980 | Herczog |
| 4,237,887 A | 12/1980 | Gosner |
| 4,253,721 A | 3/1981 | Kaufman |
| 4,281,373 A | 7/1981 | Mabille |
| 4,287,557 A | 9/1981 | Brehse |
| 4,303,073 A | 12/1981 | Archibald |
| 4,304,235 A | 12/1981 | Kaufman |
| 4,311,154 A | 1/1982 | Sterzer et al. |
| 4,314,559 A | 2/1982 | Allen |
| 4,321,926 A | 3/1982 | Roge |
| 4,331,149 A | 5/1982 | Gonser |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,381,789 A | 5/1983 | Naser et al. |
| 4,384,582 A | 5/1983 | Watt |
| 4,387,714 A | 6/1983 | Geddes et al. |
| 4,393,584 A | 7/1983 | Bare et al. |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Paterson |
| 4,643,193 A | 2/1987 | DeMarzo |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,369 A | 5/1987 | Ensslin |
| 4,662,383 A | 5/1987 | Sogawa et al. |
| 4,669,468 A | 6/1987 | Cartmell et al. |
| 4,691,703 A | 9/1987 | Auth et al. |
| 4,699,146 A | 10/1987 | Sieverding |
| 4,722,761 A | 2/1988 | Cartmell et al. |
| 4,725,713 A | 2/1988 | Lehrke |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,745,918 A | 5/1988 | Feucht |
| 4,748,983 A | 6/1988 | Shigeta et al. |
| 4,750,482 A | 6/1988 | Sieverding |
| 4,754,757 A * | 7/1988 | Feucht ..................... 606/35 |
| 4,768,514 A | 9/1988 | DeMarzo |

| | | | | | |
|---|---|---|---|---|---|
| 4,770,173 A | 9/1988 | Feucht et al. | 5,330,518 A | 7/1994 | Neilson et al. |
| 4,788,634 A | 11/1988 | Schlecht et al. | 5,334,193 A | 8/1994 | Nardella |
| 4,788,977 A | 12/1988 | Farin et al. | 5,336,255 A | 8/1994 | Kanare et al. |
| 4,799,480 A | 1/1989 | Abraham et al. | 5,341,807 A | 8/1994 | Nardella |
| 4,805,621 A | 2/1989 | Heinze et al. | 5,342,356 A | 8/1994 | Ellman |
| 4,807,621 A | 2/1989 | Hagen et al. | 5,342,357 A | 8/1994 | Nardella |
| 4,818,954 A | 4/1989 | Flachenecker et al. | 5,342,409 A | 8/1994 | Mullett |
| 4,827,927 A | 5/1989 | Newton | 5,348,554 A | 9/1994 | Imran et al. |
| 4,844,063 A | 7/1989 | Clark | 5,352,315 A | 10/1994 | Carrier et al. |
| 4,848,335 A | 7/1989 | Manes | 5,362,420 A | 11/1994 | Itoh et al. |
| 4,860,745 A | 8/1989 | Farin et al. | 5,370,645 A | 12/1994 | Klicek et al. |
| 4,862,889 A | 9/1989 | Feucht | 5,370,672 A | 12/1994 | Fowler et al. |
| 4,873,974 A | 10/1989 | Hagen et al. | 5,370,675 A | 12/1994 | Edwards et al. |
| 4,890,610 A | 1/1990 | Kirwan et al. | 5,372,596 A | 12/1994 | Klicek et al. |
| 4,895,169 A | 1/1990 | Heath | 5,383,874 A | 1/1995 | Jackson |
| 4,903,696 A | 2/1990 | Stasz et al. | 5,383,876 A | 1/1995 | Nardella |
| 4,907,589 A | 3/1990 | Cosman | 5,383,917 A | 1/1995 | Desai et al. |
| 4,922,210 A | 5/1990 | Flachenecker et al. | 5,385,148 A | 1/1995 | Lesh et al. |
| 4,931,047 A | 6/1990 | Broadwin et al. | 5,385,679 A | 1/1995 | Uy et al. |
| 4,931,717 A | 6/1990 | Gray et al. | 5,388,490 A | 2/1995 | Buck |
| 4,938,761 A | 7/1990 | Ensslin | 5,389,376 A | 2/1995 | Duan et al. |
| 4,942,313 A | 7/1990 | Kinzel | 5,390,382 A | 2/1995 | Hannant et al. |
| 4,947,846 A | 8/1990 | Kitagawa et al. | 5,400,267 A | 3/1995 | Denen et al. |
| 4,955,381 A | 9/1990 | Way et al. | 5,403,311 A | 4/1995 | Abele et al. |
| 4,961,047 A | 10/1990 | Carder | 5,403,312 A | 4/1995 | Yates et al. |
| 4,961,435 A | 10/1990 | Kitagawa et al. | 5,409,000 A | 4/1995 | Imran |
| 4,966,597 A | 10/1990 | Cosman | 5,409,485 A | 4/1995 | Suda |
| 4,969,885 A | 11/1990 | Farin | 5,409,966 A | 4/1995 | Duan et al. |
| 4,993,430 A | 2/1991 | Shimoyama et al. | 5,413,573 A | 5/1995 | Koivukangas |
| 4,995,877 A | 2/1991 | Ams et al. | 5,414,238 A | 5/1995 | Steigerwald et al. |
| 5,000,753 A | 3/1991 | Hagen et al. | 5,417,719 A | 5/1995 | Hull et al. |
| 5,004,425 A | 4/1991 | Hee | 5,422,567 A | 6/1995 | Matsunaga |
| 5,010,896 A | 4/1991 | Westbrook | 5,423,808 A | 6/1995 | Edwards et al. |
| 5,015,227 A | 5/1991 | Broadwin et al. | 5,423,809 A | 6/1995 | Klicek |
| 5,024,668 A | 6/1991 | Peters et al. | 5,423,810 A | 6/1995 | Goble et al. |
| 5,038,796 A | 8/1991 | Axelgaard et al. | 5,425,704 A | 6/1995 | Sakurai et al. |
| 5,042,981 A | 8/1991 | Gross | 5,430,434 A | 7/1995 | Lederer et al. |
| 5,061,914 A | 10/1991 | Busch et al. | 5,432,459 A | 7/1995 | Thompson |
| 5,087,257 A | 2/1992 | Farin et al. | 5,433,739 A | 7/1995 | Sluijter et al. |
| 5,103,804 A | 4/1992 | Abele et al. | 5,436,566 A | 7/1995 | Thompson |
| 5,108,389 A | 4/1992 | Cosmescu | 5,438,302 A | 8/1995 | Goble |
| 5,108,391 A | 4/1992 | Flachenecker | 5,443,463 A | 8/1995 | Stern et al. |
| 5,114,424 A | 5/1992 | Hagen et al. | 5,445,635 A | 8/1995 | Denen |
| 5,122,137 A | 6/1992 | Lennox | 5,447,513 A | 9/1995 | Davison et al. |
| 5,133,711 A | 7/1992 | Hagen | 5,449,365 A | 9/1995 | Green et al. |
| 5,151,102 A | 9/1992 | Kamiyama et al. | 5,451,224 A | 9/1995 | Goble et al. |
| 5,152,762 A | 10/1992 | McElhenney | 5,452,725 A | 9/1995 | Martenson |
| 5,157,603 A | 10/1992 | Scheller et al. | 5,458,597 A | 10/1995 | Edwards et al. |
| 5,160,334 A | 11/1992 | Billings et al. | 5,462,521 A | 10/1995 | Brucker et al. |
| 5,167,658 A | 12/1992 | Ensslin | 5,472,441 A | 12/1995 | Edwards et al. |
| 5,190,517 A | 3/1993 | Zieve et al. | 5,472,443 A | 12/1995 | Cordis et al. |
| 5,196,008 A | 3/1993 | Kuenecke et al. | 5,480,399 A | 1/1996 | Hebborn |
| 5,196,009 A | 3/1993 | Kirwan, Jr. | 5,483,952 A | 1/1996 | Aranyi |
| 5,201,900 A | 4/1993 | Nardella | 5,496,312 A | 3/1996 | Klicek |
| 5,207,691 A | 5/1993 | Nardella | 5,496,313 A | 3/1996 | Gentelia et al. |
| 5,230,623 A | 7/1993 | Guthrie et al. | 5,496,363 A | 3/1996 | Burgio et al. |
| 5,233,515 A | 8/1993 | Cosman | 5,500,012 A | 3/1996 | Brucker et al. |
| 5,246,439 A | 9/1993 | Hebborn et al. | 5,500,616 A | 3/1996 | Ochi |
| 5,249,121 A | 9/1993 | Baum et al. | 5,514,129 A | 5/1996 | Smith |
| 5,254,117 A | 10/1993 | Rigby et al. | 5,520,180 A | 5/1996 | Uy et al. |
| RE34,432 E | 11/1993 | Bertrand | 5,520,684 A | 5/1996 | Imran |
| 5,267,994 A | 12/1993 | Gentelia et al. | 5,531,774 A | 7/1996 | Schulman et al. |
| 5,267,997 A | 12/1993 | Farin | 5,534,018 A | 7/1996 | Wahlstrand et al. |
| 5,271,417 A | 12/1993 | Swanson et al. | 5,536,267 A | 7/1996 | Edwards et al. |
| 5,276,079 A | 1/1994 | Duan et al. | 5,536,446 A | 7/1996 | Uy et al. |
| 5,281,213 A | 1/1994 | Milder et al. | 5,540,681 A | 7/1996 | Strul et al. |
| 5,286,255 A | 2/1994 | Weber | 5,540,683 A | 7/1996 | Ichikawa |
| 5,300,068 A | 4/1994 | Rosar et al. | 5,540,684 A | 7/1996 | Hassler, Jr. |
| 5,300,070 A | 4/1994 | Gentelia | 5,556,396 A | 9/1996 | Cohen et al. |
| 5,312,401 A | 5/1994 | Newton et al. | 5,558,671 A | 9/1996 | Yates |
| 5,318,563 A | 6/1994 | Malis et al. | 5,569,242 A | 10/1996 | Lax et al. |
| 5,323,778 A | 6/1994 | Kandarpa et al. | 5,571,147 A | 11/1996 | Sluijter et al. |
| 5,324,283 A | 6/1994 | Heckele | 5,573,533 A | 11/1996 | Strul |

| | | | | | |
|---|---|---|---|---|---|
| 5,584,830 A | 12/1996 | Ladd et al. | 5,924,983 A | 7/1999 | Takaki et al. |
| 5,588,432 A | 12/1996 | Crowley | 5,925,070 A | 7/1999 | King et al. |
| 5,596,466 A | 1/1997 | Ochi | 5,931,836 A | 8/1999 | Hatta et al. |
| 5,599,344 A | 2/1997 | Paterson | 5,938,690 A | 8/1999 | Law et al. |
| 5,599,345 A | 2/1997 | Edwards et al. | 5,947,961 A | 9/1999 | Netherly |
| 5,599,347 A | 2/1997 | Hart et al. | 5,948,007 A | 9/1999 | Starkebaum et al. |
| 5,599,348 A | 2/1997 | Gentelia et al. | 5,951,545 A | 9/1999 | Schilling |
| 5,601,618 A | 2/1997 | James | 5,951,546 A | 9/1999 | Lorentzen |
| 5,605,150 A | 2/1997 | Radons et al. | 5,952,398 A | 9/1999 | Dietz et al. |
| 5,611,709 A | 3/1997 | McAnulty | 5,954,686 A | 9/1999 | Garito et al. |
| 5,613,966 A | 3/1997 | Makower et al. | 5,954,717 A | 9/1999 | Behl et al. |
| 5,626,575 A | 5/1997 | Crenner | 5,954,719 A | 9/1999 | Chen et al. |
| 5,628,745 A | 5/1997 | Bek | 5,961,344 A | 10/1999 | Rosales et al. |
| 5,632,280 A | 5/1997 | Leyde et al. | 5,971,980 A | 10/1999 | Sherman |
| 5,643,319 A | 7/1997 | Green et al. | 5,971,981 A | 10/1999 | Hill et al. |
| 5,643,330 A | 7/1997 | Holsheimer et al. | 5,976,128 A | 11/1999 | Schilling et al. |
| 5,647,869 A | 7/1997 | Goble et al. | 5,983,141 A | 11/1999 | Sluijter et al. |
| 5,647,871 A | 7/1997 | Levine et al. | 5,985,990 A | 11/1999 | Kantner et al. |
| 5,651,780 A | 7/1997 | Jackson et al. | 5,999,061 A | 12/1999 | Pope et al. |
| 5,658,322 A | 8/1997 | Fleming | 6,007,532 A | 12/1999 | Netherly |
| 5,660,567 A | 8/1997 | Nierlich et al. | 6,010,054 A | 1/2000 | Johnson et al. |
| 5,660,892 A | 8/1997 | Robbins et al. | 6,010,499 A | 1/2000 | Cobb |
| 5,670,557 A | 9/1997 | Dietz et al. | 6,014,581 A | 1/2000 | Whayne et al. |
| 5,674,217 A | 10/1997 | Wahlstrom et al. | 6,030,381 A | 2/2000 | Jones et al. |
| 5,674,561 A | 10/1997 | Dietz et al. | 6,032,063 A | 2/2000 | Hoar et al. |
| 5,678,545 A | 10/1997 | Stratbucker | 6,033,399 A | 3/2000 | Gines |
| 5,685,840 A | 11/1997 | Schechter et al. | 6,039,732 A | 3/2000 | Ichikawa et al. |
| 5,688,267 A | 11/1997 | Panescu et al. | 6,044,283 A | 3/2000 | Fein et al. |
| 5,688,269 A | 11/1997 | Newton et al. | 6,053,910 A | 4/2000 | Fleenor |
| 5,693,042 A | 12/1997 | Boiarski et al. | 6,053,912 A | 4/2000 | Panescu et al. |
| 5,694,304 A | 12/1997 | Telefus et al. | 6,055,458 A | 4/2000 | Cochran et al. |
| 5,695,494 A | 12/1997 | Becker | RE36,720 E | 5/2000 | Green et al. |
| 5,702,386 A | 12/1997 | Stern et al. | 6,056,745 A | 5/2000 | Panescu et al. |
| 5,702,429 A | 12/1997 | King | 6,056,746 A | 5/2000 | Goble et al. |
| 5,707,369 A | 1/1998 | Vaitekunas et al. | 6,059,778 A | 5/2000 | Sherman |
| 5,712,772 A | 1/1998 | Telefus et al. | 6,063,075 A | 5/2000 | Mihori |
| 5,713,896 A | 2/1998 | Nardella | 6,063,078 A | 5/2000 | Wittkampf |
| 5,718,719 A | 2/1998 | Clare et al. | 6,068,627 A | 5/2000 | Orszulak et al. |
| 5,720,744 A | 2/1998 | Eggleston et al. | 6,074,386 A | 6/2000 | Goble et al. |
| 5,722,975 A | 3/1998 | Edwards et al. | 6,074,388 A | 6/2000 | Tockweiler et al. |
| 5,733,281 A | 3/1998 | Nardella | 6,080,149 A | 6/2000 | Huang et al. |
| 5,749,869 A | 5/1998 | Lindenmeier et al. | 6,083,221 A | 7/2000 | Fleenor et al. |
| 5,749,871 A | 5/1998 | Hood et al. | 6,086,249 A | 7/2000 | Urich |
| 5,755,715 A | 5/1998 | Stern | 6,093,186 A | 7/2000 | Goble |
| 5,766,165 A | 6/1998 | Gentelia et al. | 6,102,497 A | 8/2000 | Ehr et al. |
| 5,769,847 A | 6/1998 | Panescu | 6,113,591 A | 9/2000 | Whayne et al. |
| 5,772,659 A | 6/1998 | Becker et al. | 6,113,596 A | 9/2000 | Hooven |
| 5,779,632 A | 7/1998 | Dietz et al. | 6,121,508 A | 9/2000 | Bischof et al. |
| 5,792,138 A | 8/1998 | Shipp | 6,123,702 A | 9/2000 | Swanson et al. |
| 5,797,902 A | 8/1998 | Netherly | 6,132,429 A | 10/2000 | Baker |
| 5,800,426 A | 9/1998 | Taki et al. | 6,135,953 A | 10/2000 | Carim |
| 5,814,092 A | 9/1998 | King | 6,142,992 A | 11/2000 | Cheng et al. |
| 5,817,091 A | 10/1998 | Nardella et al. | 6,155,975 A | 12/2000 | Urich et al. |
| 5,817,093 A | 10/1998 | Williamson, IV et al. | 6,162,217 A | 12/2000 | Kannenberg et al. |
| 5,820,568 A | 10/1998 | Willis | 6,171,304 B1 | 1/2001 | Netherly et al. |
| 5,827,271 A | 10/1998 | Buysse et al. | 6,200,314 B1 | 3/2001 | Sherman |
| 5,830,212 A | 11/1998 | Cartmell et al. | 6,203,541 B1 | 3/2001 | Keppel |
| 5,836,909 A | 11/1998 | Cosmescu | 6,210,403 B1 | 4/2001 | Klicek |
| 5,836,942 A | 11/1998 | Netherly et al. | 6,214,000 B1 | 4/2001 | Fleenor et al. |
| 5,836,943 A | 11/1998 | Miller, III | 6,228,080 B1 | 5/2001 | Gines |
| 5,836,990 A | 11/1998 | Li | 6,228,081 B1 | 5/2001 | Goble |
| 5,846,236 A | 12/1998 | Lindenmeier et al. | 6,231,569 B1 | 5/2001 | Bek |
| 5,846,558 A | 12/1998 | Nielsen et al. | 6,232,366 B1 | 5/2001 | Wang et al. |
| 5,853,750 A | 12/1998 | Dietz et al. | 6,235,020 B1 | 5/2001 | Cheng et al. |
| 5,868,737 A | 2/1999 | Taylor et al. | 6,238,387 B1 | 5/2001 | Miller, III |
| 5,868,739 A | 2/1999 | Lindenmeier et al. | 6,238,388 B1 | 5/2001 | Ellman |
| 5,868,740 A | 2/1999 | LeVeen et al. | 6,240,323 B1 | 5/2001 | Calenzo, Sr. et al. |
| 5,868,742 A | 2/1999 | Manes et al. | 6,241,725 B1 | 6/2001 | Cosman |
| 5,871,481 A | 2/1999 | Kannenberg et al. | 6,245,065 B1 | 6/2001 | Panescu |
| 5,897,552 A | 4/1999 | Edwards et al. | 6,246,912 B1 | 6/2001 | Sluijter et al. |
| 5,908,444 A | 6/1999 | Azure | 6,251,106 B1 | 6/2001 | Becker et al. |
| 5,913,882 A | 6/1999 | King | 6,258,085 B1 | 7/2001 | Eggleston |
| 5,921,982 A | 7/1999 | Lesh et al. | 6,261,285 B1 | 7/2001 | Novak |

| | | |
|---|---|---|
| 6,261,286 B1 | 7/2001 | Goble et al. |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,296,636 B1 | 10/2001 | Cheng et al. |
| 6,301,500 B1 | 10/2001 | Van Herk et al. |
| 6,306,131 B1 | 10/2001 | Hareyama et al. |
| 6,306,134 B1 | 10/2001 | Goble et al. |
| 6,309,386 B1 | 10/2001 | Bek |
| 6,310,611 B1 | 10/2001 | Caldwell |
| 6,325,799 B1 | 12/2001 | Goble |
| 6,337,998 B1 | 1/2002 | Behl et al. |
| 6,338,657 B1 | 1/2002 | Harper et al. |
| 6,347,246 B1 | 2/2002 | Perrault et al. |
| 6,350,262 B1 | 2/2002 | Ashley |
| 6,350,264 B1 | 2/2002 | Hooven |
| 6,357,089 B1 | 3/2002 | Koguchi et al. |
| 6,358,245 B1 | 3/2002 | Edwards et al. |
| 6,364,877 B1 | 4/2002 | Goble et al. |
| 6,379,161 B1 | 4/2002 | Ma |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,743 B1 | 6/2002 | Orszulak et al. |
| 6,409,722 B1 | 6/2002 | Hoey et al. |
| 6,413,255 B1 | 7/2002 | Stern |
| 6,415,170 B1 | 7/2002 | Loutis et al. |
| 6,416,509 B1 | 7/2002 | Goble et al. |
| 6,436,096 B1 | 8/2002 | Hareyama |
| 6,451,015 B1 | 9/2002 | Rittman, III et al. |
| 6,454,764 B1 | 9/2002 | Fleenor et al. |
| 6,458,121 B1 | 10/2002 | Rosenstock |
| 6,464,689 B1 | 10/2002 | Qin |
| 6,464,696 B1 | 10/2002 | Oyama |
| 6,488,678 B2 | 12/2002 | Sherman |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,524,308 B1 | 2/2003 | Muller et al. |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,547,786 B1 | 4/2003 | Goble |
| 6,558,376 B2 | 5/2003 | Bishop |
| 6,562,037 B2 | 5/2003 | Paton |
| 6,565,559 B2 | 5/2003 | Eggleston |
| 6,569,160 B1 | 5/2003 | Goldin et al. |
| 6,575,969 B1 | 6/2003 | Rittman, III et al. |
| 6,582,424 B2 | 6/2003 | Fleenor et al. |
| 6,582,427 B1 | 6/2003 | Goble et al. |
| 6,620,157 B1 | 9/2003 | Dabney et al. |
| 6,623,423 B2 | 9/2003 | Sakurai |
| 6,635,057 B2 | 10/2003 | Harano |
| 6,648,883 B2 | 11/2003 | Francischelli |
| 6,652,514 B2 | 11/2003 | Ellman |
| 6,663,623 B1 | 12/2003 | Oyama et al. |
| 6,663,624 B2 | 12/2003 | Edwards |
| 6,666,859 B1 | 12/2003 | Fleenor et al. |
| 6,666,860 B1 | 12/2003 | Takahashi |
| 6,669,073 B2 | 12/2003 | Milliman et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,692,489 B1 | 2/2004 | Heim |
| 6,712,813 B2 | 3/2004 | Ellman |
| 6,730,080 B2 | 5/2004 | Harano |
| 6,733,495 B1 | 5/2004 | Bek |
| 6,733,498 B2 | 5/2004 | Paton |
| 6,736,810 B2 | 5/2004 | Hoey et al. |
| 6,740,079 B1 | 5/2004 | Eggers |
| 6,740,085 B2 | 5/2004 | Hareyama |
| 6,783,523 B2 | 8/2004 | Qin |
| 6,786,905 B2 | 9/2004 | Swanson et al. |
| 6,790,206 B2 | 9/2004 | Panescu |
| 6,796,828 B2 | 9/2004 | Ehr et al. |
| 6,796,981 B2 | 9/2004 | Wham |
| 6,799,063 B2 | 9/2004 | Carson |
| 6,824,539 B2 | 11/2004 | Novak |
| 6,830,569 B2 | 12/2004 | Thompson et al. |
| 6,843,789 B2 | 1/2005 | Goble |
| 6,849,073 B2 | 2/2005 | Hoey et al. |
| 6,855,141 B2 | 2/2005 | Lovewell |
| 6,855,142 B2 | 2/2005 | Harano |
| 6,860,881 B2 | 3/2005 | Sturm et al. |
| 6,864,686 B2 | 3/2005 | Novak |
| 6,875,210 B2 | 4/2005 | Refior et al. |
| 6,892,086 B2 | 5/2005 | Russell |
| 6,893,435 B2 | 5/2005 | Goble |
| 6,905,497 B2 | 6/2005 | Truckai et al. |
| 6,939,344 B2 | 9/2005 | Kreindel |
| 6,948,503 B2 | 9/2005 | Refior et al. |
| 6,953,139 B2 | 10/2005 | Milliman et al. |
| 6,959,852 B2 | 11/2005 | Shelton, IV et al. |
| 6,997,735 B2 | 2/2006 | Ehr et al. |
| 7,025,765 B2 | 4/2006 | Balbierz et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,063,692 B2 | 6/2006 | Sakurai et al. |
| 7,066,933 B2 | 6/2006 | Hagg |
| 7,128,253 B2 | 10/2006 | Mastri et al. |
| 7,131,860 B2 | 11/2006 | Sartor et al. |
| 7,137,980 B2 | 11/2006 | Buysse et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,172,591 B2 | 2/2007 | Harano et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,247,155 B2 | 7/2007 | Hoey et al. |
| 7,255,694 B2 | 8/2007 | Keppel |
| 7,258,262 B2 | 8/2007 | Mastri et al. |
| 7,267,675 B2 | 9/2007 | Stern et al. |
| 7,278,562 B2 | 10/2007 | Mastri et al. |
| 7,300,435 B2 | 11/2007 | Wham et al. |
| 7,303,107 B2 | 12/2007 | Milliman et al. |
| 7,303,557 B2 | 12/2007 | Wham et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 7,473,145 B2 | 1/2009 | Ehr et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |

| | | |
|---|---|---|
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0147918 A1 | 7/2004 | Keppel |
| 2004/0150504 A1 | 8/2004 | Nicholson |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0021020 A1 | 1/2005 | Blaha et al. |
| 2005/0021022 A1 | 1/2005 | Sturm et al. |
| 2005/0085806 A1 | 4/2005 | Auge, II et al. |
| 2005/0101947 A1* | 5/2005 | Jarrard et al. ................ 606/35 |
| 2005/0101949 A1 | 5/2005 | Harano et al. |
| 2005/0101951 A1 | 5/2005 | Wham |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2005/0251130 A1 | 11/2005 | Boveja et al. |
| 2006/0025760 A1 | 2/2006 | Podhajsky |
| 2006/0041251 A1 | 2/2006 | Odell et al. |
| 2006/0041252 A1 | 2/2006 | Odell et al. |
| 2006/0041253 A1 | 2/2006 | Newton et al. |
| 2006/0074411 A1 | 4/2006 | Carmel et al. |
| 2006/0079871 A1 | 4/2006 | Plaven et al. |
| 2006/0079872 A1 | 4/2006 | Eggleston |
| 2006/0161148 A1 | 7/2006 | Behnke |
| 2006/0173250 A1 | 8/2006 | Nessler |
| 2006/0178664 A1 | 8/2006 | Keppel |
| 2006/0217742 A1 | 9/2006 | Messerly et al. |
| 2006/0224150 A1 | 10/2006 | Arts et al. |
| 2006/0224152 A1 | 10/2006 | Behnke et al. |
| 2006/0281360 A1 | 12/2006 | Sartor et al. |
| 2007/0038209 A1 | 2/2007 | Buysse et al. |
| 2007/0049914 A1 | 3/2007 | Eggleston |
| 2007/0049916 A1 | 3/2007 | Isaacson et al. |
| 2007/0049919 A1 | 3/2007 | Lee, Jr. et al. |
| 2007/0073284 A1 | 3/2007 | Sturm et al. |
| 2007/0074719 A1 | 4/2007 | Danek et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0161979 A1 | 7/2007 | McPherson |
| 2007/0167942 A1 | 7/2007 | Rick |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0203481 A1 | 8/2007 | Gregg et al. |
| 2007/0208339 A1 | 9/2007 | Arts et al. |
| 2007/0225698 A1 | 9/2007 | Orszulak et al. |
| 2007/0244478 A1 | 10/2007 | Bahney |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0009846 A1 | 1/2008 | Ward |
| 2008/0033276 A1 | 2/2008 | Ehr et al. |
| 2008/0083806 A1 | 4/2008 | Scirica |
| 2008/0083813 A1 | 4/2008 | Zemlok et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3206947 | 9/1983 |
| DE | 3510586 | 10/1986 |
| DE | 3544443 | 6/1987 |
| DE | 3604823 | 8/1987 |
| DE | 390937 | 4/1989 |
| DE | 3904558 | 8/1990 |
| DE | 3942998 | 7/1991 |
| DE | 42 38 263 A1 | 5/1993 |
| DE | 4231236 | 3/1994 |
| DE | 4339049 | 5/1995 |
| DE | 197 17 411 A1 | 11/1998 |
| DE | 19717411 | 11/1998 |
| DE | 198 01 173 | 7/1999 |
| DE | 19848540 | 5/2000 |
| DE | 103 28 514 | 6/2003 |
| DE | 102004010940 | 9/2005 |
| EP | 246350 | 11/1987 |
| EP | 0262888 | 4/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |

| | | |
|---|---|---|
| EP | 608609 | 8/1994 |
| EP | 0694291 | 1/1996 |
| EP | 836868 | 4/1998 |
| EP | 878169 | 11/1998 |
| EP | 0 930 048 | 7/1999 |
| EP | 1 051 949 | 11/2000 |
| EP | 1051948 | 11/2000 |
| EP | 1076350 | 2/2001 |
| EP | 1151725 | 11/2001 |
| EP | 1293171 | 3/2003 |
| EP | 1 468 653 | 10/2004 |
| EP | 1495712 | 1/2005 |
| EP | 1500378 | 1/2005 |
| EP | 1535581 | 6/2005 |
| EP | 1 645 236 | 4/2006 |
| EP | 880220 | 6/2006 |
| EP | 1707143 | 10/2006 |
| EP | 1707151 | 10/2006 |
| EP | 1 808 144 | 7/2007 |
| EP | 1810630 | 7/2007 |
| EP | 1902684 | 3/2008 |
| FR | 1275415 | 10/1961 |
| FR | 1347865 | 11/1963 |
| FR | 2.276.027 | 6/1974 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 2 054 382 | 2/1981 |
| GB | 2164473 | 3/1986 |
| GB | 2214430 | 9/1989 |
| GB | 2358934 | 8/2001 |
| GB | 2374532 | 10/2002 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO02/11634 | 2/2002 |
| WO | WO02/45589 | 6/2002 |
| WO | WO02/47565 | 6/2002 |
| WO | WO02/088128 | 7/2002 |
| WO | WO 02/058579 | 8/2002 |
| WO | WO 02/060526 | 8/2002 |
| WO | WO 02/099442 | 12/2002 |
| WO | WO03/092520 | 11/2003 |
| WO | WO 03/094766 | 11/2003 |
| WO | WO2003/090635 | 11/2003 |
| WO | WO2005/060365 | 11/2003 |
| WO | WO 2004/028385 | 4/2004 |
| WO | WO2004/028385 | 4/2004 |
| WO | WO2004/098385 | 4/2004 |
| WO | WO 2004/074854 | 9/2004 |
| WO | WO2005/046496 | 5/2005 |
| WO | WO2005/048809 | 6/2005 |
| WO | WO 2005/048809 | 6/2005 |
| WO | WO2005/050151 | 6/2005 |
| WO | WO2005/060849 | 7/2005 |
| WO | WO 2005/087124 | 9/2005 |
| WO | WO 2005/099606 | 10/2005 |
| WO | WO 2005/110263 | 11/2005 |
| WO | WO 2008/009385 | 1/2008 |

OTHER PUBLICATIONS

International Search Report EP 07010673.7, dated Sep. 24, 2007.
International Search Report EP 05021944.3 dated Jan. 25, 2006.
International Search Report EP 05002027.0 dated May 12, 2005.
International Search Report EP 06006961 dated Aug. 3, 2006.
International Search Report EP 07000885.9 dated May 15, 2007.
International Search Report PCT/US2004/004196 dated Oct. 4, 2007.
International Search Report EP06006961.4 dated Oct. 5, 2007.
International Search Report EP07000885.9 dated May 2, 2007.
International Search Report EP07007783.9 dated Aug. 6, 2007.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52, No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. Mi, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.

Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP07000567.3 dated Dec. 3, 2008.
International Search Report EP08006731 dated Jul. 14, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152130.2 dated Apr. 6, 2009.

* cited by examiner

SYSTEM AND METHOD FOR RETURN ELECTRODE MONITORING

BACKGROUND

1. Technical Field

The present disclosure relates generally to a system and method for using a plurality of return electrodes during electrosurgery and, more particularly, to a system and method for balancing the various thermal effects of the plurality of return electrodes by minimizing the probability of tissue damage and ensuring the plurality of return electrodes are properly attached to a patient.

2. Background of Related Art

During electrosurgery, a source or active electrode delivers energy, such as radio frequency (RF) energy, from an electrosurgical generator to a patient and a return electrode or a plurality thereof carry current back to the electrosurgical generator. In monopolar electrosurgery, the source electrode is typically a hand-held instrument placed by the user at the surgical site and the high current density flow at this electrode creates the desired surgical effect of ablating, cutting or coagulating tissue. The patient return electrodes are placed at a remote site from the source electrode and are typically in the form of pads adhesively adhered to the patient.

The return electrodes usually have a large patient contact surface area to minimize heating at that site since the smaller the surface area, the greater the current density and the greater the intensity of the heat. That is, the area of the return electrode that is adhered to the patient is important because it is the current density of the electrical signal that heats the tissue. A larger surface contact area is desirable to reduce heat intensity. Return electrodes are sized based on assumptions of the maximum current seen in surgery and the duty cycle (i.e., the percentage of time the generator is on) during the procedure.

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heat applied to the tissue. This risked burning the patient in the area under the adhered portion of the return electrode if the tissue was heated beyond the point where circulation of blood could cool the skin.

To address this problem, split return electrodes and hardware circuits, generically called return electrode contact quality monitors (RECQMs), were developed. These split electrodes consist of two separate conductive foils. The hardware circuit uses an AC signal between the two electrode halves to measure the impedance therebetween. This impedance measurement is indicative of how well the return electrode is adhered to the patient since the impedance between the two halves is directly related to the area of patient contact with the return electrode. That is, if the electrode begins to peel from the patient, the impedance increases since the contact area of the electrode decreases. Current RECQMs are designed to sense this change in impedance so that when the percentage increase in impedance exceeds a predetermined value or the measured impedance exceeds a threshold level, the electrosurgical generator is shut down to reduce the chances of burning the patient.

Currently, during electrosurgical procedures involving especially high current, it is common to use multiple return electrodes to ensure adequate surface area to minimize heating at the return electrodes and thereby minimize the risk of damaging tissue. Typical ablation procedures can deliver up to 2.0 $A_{rms}$ for up to 20 minutes either continuously or with periodic current pulses. This extended duration for a high total current value may create a potential for alternate site burns due to return electrode pad heating. Further, the use of multiple return electrodes may also pose an additional potential problem—the increase in temperature under each of the return electrodes is not uniform, e.g., there is a thermal imbalance among the multiple return electrodes. This is caused by the differing impedance values between the active electrode and each of the multiple return electrodes, which varies due to placement and proximity of the active electrode to the return electrode.

Typically, since current is the primary factor in return electrode heating, measurement of the total current output from the electrosurgical generator may be used to infer possible tissue damage. Although the total current output of the electrosurgery generator is approximately equal to the sum of the current through each of the return electrodes, the individual return electrode currents may not be equal due to the differing impedances as described above. This condition may generate an imbalance of current among each of the return electrodes resulting in an imbalance of thermal rise on the return electrodes.

SUMMARY

Systems and methods for ensuring the plurality of return electrodes are properly attached to a patient, balancing thermal effects, and reducing probability of tissue damage during electrosurgical procedures involving a multitude of return electrodes are disclosed. More specifically, the system includes an electrosurgical generator and a plurality of return electrodes as well as a current monitor, a switch, and an impedance sensor electrically connected to each of the return electrodes and the electrosurgical generator. The generator monitors the current passing through each of the return electrodes through the current monitor. The generator determines current load ratio for each return electrode to ensure the return electrodes are properly attached to patient.

According to one embodiment of the present disclosure, a system for monitoring a plurality of return electrodes is disclosed. The system includes an electrosurgical generator adapted to generate an electrosurgical current and a plurality of return electrodes adhered to a patient and adapted to couple to the electrosurgical generator. The system also includes a current monitor connected in series with each of the plurality of the return electrodes to measure a current signal passing therethrough and a processor coupled to each of the current monitors. The processor is configured to determine a desired current ratio and an actual current ratio for each of the plurality of the return electrodes as a function of the current passing through each of the plurality of the return electrodes. The processor is further configured to compare the desired current ratio and the actual current ratio.

According to another embodiment of the present disclosure, a method for monitoring a plurality of return electrodes is disclosed. The method includes the step of providing a plurality of return electrodes adhered to a patient and coupled to an electrosurgical generator configured to generate an electrosurgical current and a current monitor connected in series with each of the plurality of the return electrodes. The method also includes the steps of determining a desired current ratio for each of the plurality of the return electrodes and measuring a current passing through each of the plurality of the return electrodes. The method further includes the steps of determining an actual current ratio as a function of the current passing through each of the plurality of the return electrodes and comparing the desired current ratio and the actual current ratio.

BRIEF DESCRIPTION OF THE DRAWINGS

The above and other aspects, features and advantages of the present disclosure will become more apparent in light of the following detailed description in conjunction with the accompanying drawings in which.

DETAILED DESCRIPTION

Embodiments of the present disclosure are described hereinbelow with reference to the accompanying drawings. In the following description, well-known functions or constructions are not described in detail to avoid obscuring the present disclosure in unnecessary detail.

Systems and methods for determining whether return electrodes are properly attached to a patient, for balancing thermal effects of multiple return electrodes, and for preventing tissue damage when using multiple return electrodes are disclosed.

Figure 1:
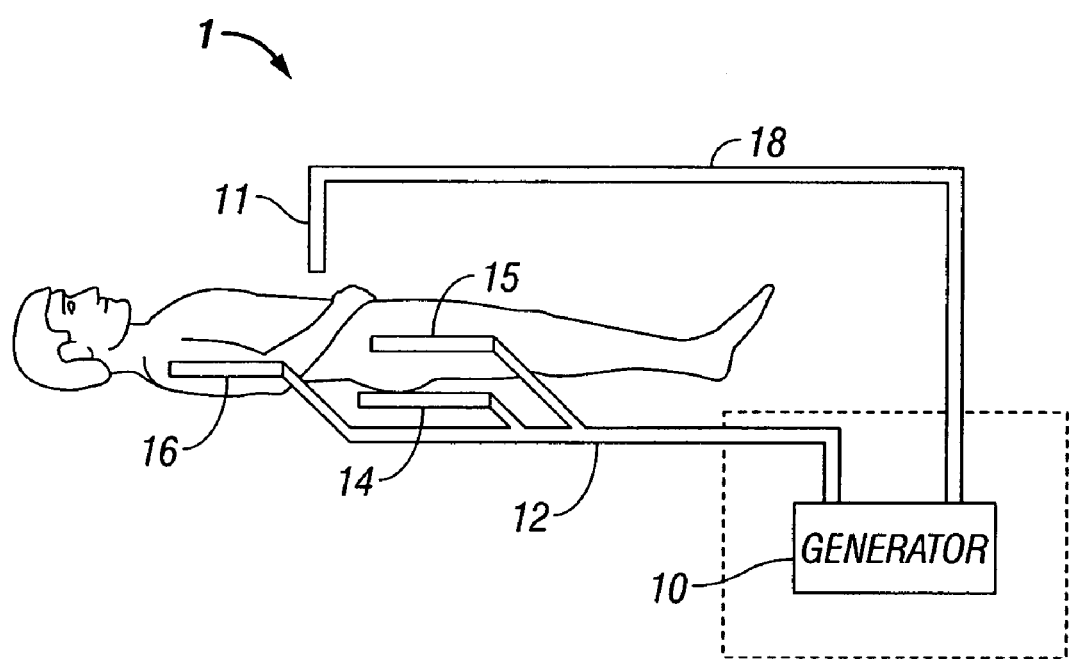
FIG. 1 is a schematic illustration of a monopolar electrosurgical system.

FIG. 1 is a schematic illustration of a monopolar electrosurgical system 1. The system 1 includes a surgical instrument 11, e.g., an active electrode, for treating tissue at a surgical site. Electrosurgical energy is supplied to the instrument 11 by a generator 10 via a cable 18 allowing the instrument 11 to ablate, cut or coagulate the tissue. The electrosurgical system also includes a plurality of return electrodes 14, 15 and 16 placed under the patient's back, the patient's leg, and the patient's arm, respectively, to return the energy from the patient to the generator 10 via a cable 12. The return electrodes 14, 15 and 16 are preferably in the form of a split pad which is adhesively attached to the patient's skin.

The surface area of the return electrodes 14, 15 and 16 that adheres to the patient is substantially similar since the surface area affects the current density of the signal which, in turn, heats the tissue. The smaller the contact area of the return electrode with the patient's tissue, the greater the current density and concentrated heating of tissue underneath the return electrodes 14, 15 and 16. Conversely, the greater the contact area of the return electrodes 14, 15 and 16, the smaller the current density and the less heating of tissue.

Figure 2:
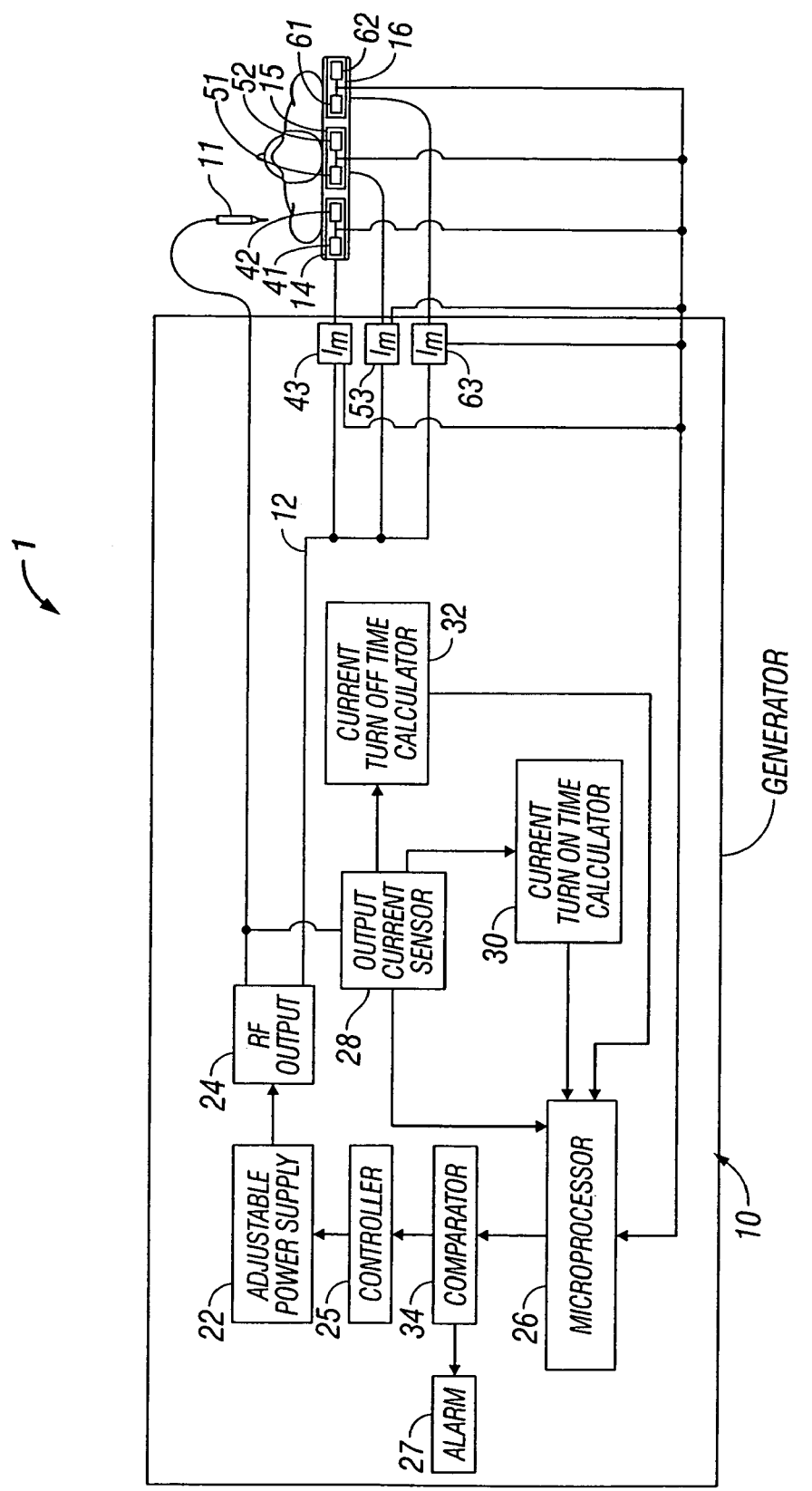
FIG. 2 is a schematic block diagram of an electrosurgical system for determining adherence of multiple return electrodes to a patient.

FIG. 2 illustrates a schematic block diagram of the electrosurgical system 1 for determining whether the return electrodes 14, 15 and 16 are properly adhered to the patient's body. The system 1 includes generator 10 for generating electrosurgical energy, an active electrode 11, e.g., an instrument, for delivering the electrosurgical energy to the tissue and a plurality of return electrodes 14, 15 and 16 for receiving the electrosurgical energy and returning the electrosurgical energy to the generator 10. Although the present disclosure describes the electrosurgical system 1 in reference to three return electrodes 14, 15 and 16, those skilled in the relevant art will understand that the principles of the present disclosure may be used with any number of return electrodes.

The generator 10 includes a microprocessor 26, an adjustable power supply 22, such as a high voltage supply coupled to an RF output stage 24 which generates RF energy for transmission to the instrument 11. The microprocessor 26 includes a plurality of input ports. A first input port in electrical communication with an output current sensor 28 measures the output current being transmitted to the patient through the instrument 11.

The return electrodes 14, 15 and 16 are electrically connected to the generator 10 through the cable 12 and in series to current monitors 43, 53 and 63, which are connected to the microprocessor 26 and report the current passing through the respective return electrodes 14, 15 and 16. When using multiple return electrodes, monitoring the total current output by the generator 10 may not be accurate in measuring the current passing through each of the return electrodes 14, 15 and 16. Therefore, the system according to the present disclosure places the current monitors 43, 53 and 63 in series with the corresponding return electrodes 14, 15 and 16 to allow accurate current measurements.

Figure 3:
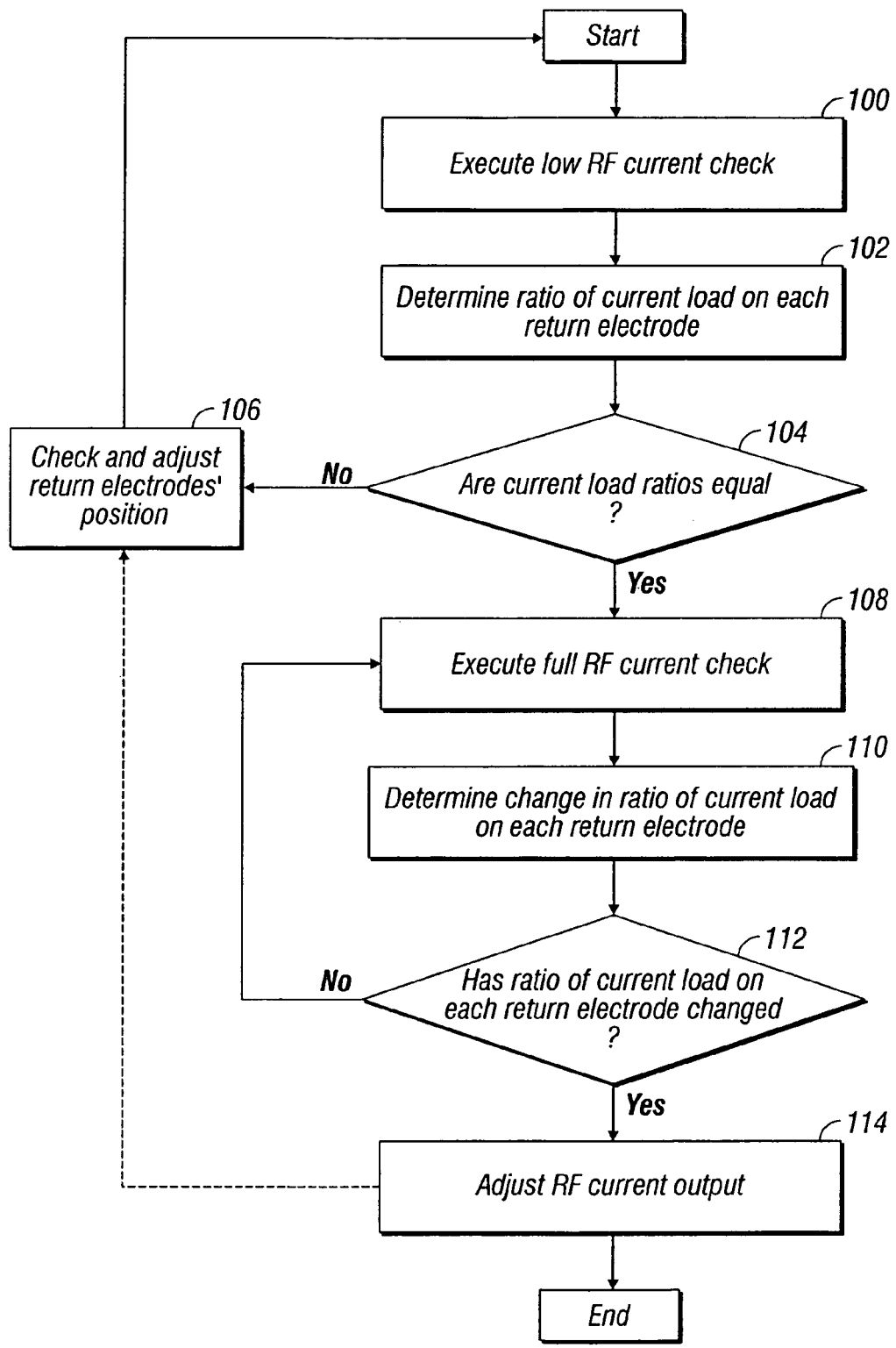
FIG. 3 is a flow diagram showing a method for determining adherence of multiple return electrodes to a patient.

FIG. 3 shows a method for determining adherence of multiple return electrode pads to a patient. This is accomplished by determining the ratios of the current load on each of the return electrodes 14, 15 and 16. Ideally, the return electrodes 14, 15 and 16 are of the same size and made from the same material. In absence of interference from other variables affecting impedance (e.g., temperature, moisture, etc.), the current load on each return electrode is the same since their impedance is the same. Alternatively, pads of different size or shape can be used with adjustment made to the allowable ratio. Current load is determined by calculating the ratio of the current distribution on each of the return electrodes 14, 15 and 16. For instance, if there are three return electrodes (e.g., the return electrodes 14, 15 and 16) then the ratio of the current load on each of the return electrodes should be 33% (i.e., total current divided by the number of return electrodes—current passing through each return electrode is 33% of the total current output). If that ratio changes, it follows that the current load is distributed unevenly. This is caused by differing impedance of each of the return electrodes or tissue between the active electrode and each respective return electrode. Since all of the return electrodes are of the same size and material, the differing impedances are caused by the placements and/or adherence of the return electrodes. Hence, determining the ratios of the current load allows the system to determine whether the return electrodes 14, 15 and 16 are placed properly on the patient and are properly adhered thereto.

The presently disclosed process verifies the ratios at two stages: first, prior to commencement of an electrosurgical procedure, and second, during the procedure. In step 100, an initial check of adherence of the return electrodes 14, 15 and 16 is performed. The return electrodes 14, 15 and 16 are placed on the patient and the generator 10 is activated. The generator 10 outputs a low level interrogation current to calculate the baseline ratio for each of the return electrodes 14, 15 and 16. A low level interrogation current is used since the method initially verifies the placement and adherence of the return electrodes 14, 15 and 16 prior to commencement of electrosurgery. Current is measured by the current monitors 43, 53 and 63 and the measurements are transmitted to the microprocessor 26.

In step 102, the generator 10 determines the percentage of total current passing through each return electrode 14, 15 and 16 and compares the calculated values to the preferred ratio (e.g., 33%). In step 104, the generator 10 determines if the current load ratios of the return electrodes 14, 15 and 16 are equal (i.e., larger or smaller than 33%). The ratios may be considered equal if they fall within a predetermined threshold. For instance, if the ratio denoting that the return electrode is properly adhered to the patient is 33% and the actual ratio (e.g., 31%) is within a predetermined threshold (e.g., 2%), the two ratios are considered equal. This eliminates the probability of insignificant changes in the current load affecting the comparison process.

If the ratios are not equal, then the generator 10 (e.g., microprocessor 26) signals that the placement of the return electrodes 14, 15 and 16 needs to be checked and adjusted if required in step 106. After readjustment, in step 106, the generator 10 outputs low interrogation current again, to verify that the readjustment corrected the problem. The process loops until the ratios of the current load of each of in the return electrodes 14, 15 and 16 are equal or within a predetermine tolerance.

If the ratios of the current load are equal, then the process continues to step 108, wherein a second check of the ratios is performed as RF energy is supplied to the tissue and returned via the return electrodes 14, 15 and 16. The current monitors 43, 53 and 63 measure the current passing through the return electrodes 14, 15 and 16 throughout the procedure and transmit the measurements to the generator 10. In step 110, the generator 10 again determines the percentage of total current passing through each return electrode 14, 15 and 16 and compares the calculated values to the preferred ratio (e.g., 33%).

In step 112, the generator 10 determines if the current load ratios of the return electrodes 14, 15 and 16 has changed from the baseline measurements taken prior to commencement of the electrosurgical procedure by comparing the measured current ratio to the preferred current ratio. If the ratios have changed, the algorithm of the generator 10 assumes that the positioning of the return electrodes 14, 15 and 16 has also changed since the last check of the ratios in step 104. If there is a change, in step 114 the generator 10 adjusts the RF current output or shuts down. The action taken by the generator 10 depends on the degree in the change. A relatively small change in the ratio (e.g., below 5% for a three return electrode system) may require an adjustment in the RF energy output. This may be accomplished using switches (e.g., switches 44, 54 and 64 shown in FIG. 4 and described in more detail below). A large change in the ratio (e.g., 5% or more) may require shutting down the generator 10. If the generator 10 shuts down, then the process proceeds to step 106, which is an optional step, where adjustments to the placement and positioning of the return electrodes 14, 15 and 16 are made.

If the ratios are unchanged as determined in step 112, then the process loops to step 108, where the ratio is continually verified during the electrosurgical procedure. This process ensures that the return electrodes 14, 15 and 16, are properly attached to the patient prior to and during electrosurgery, thereby allowing the RF energy to be efficiently dissipated.

Figure 4:
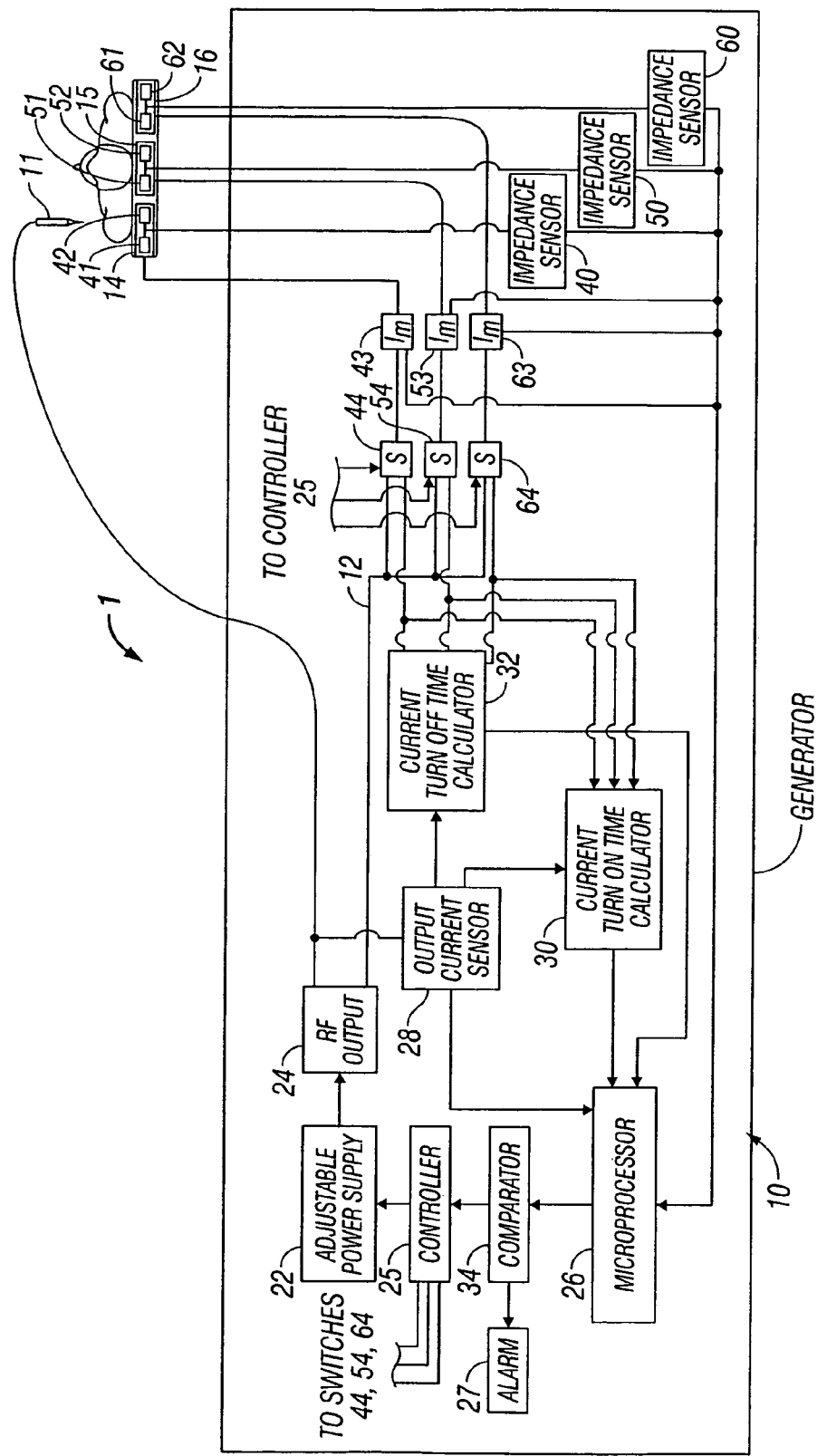
FIG. 4 is a schematic block diagram of on electrosurgical system for determining the probability of tissue damage and controlling return current in multiple return electrodes.

FIG. 4 illustrates a schematic block diagram of the electrosurgical system 1 for determining the probability of tissue damage and controlling the return current in multiple return electrodes 14, 15 and 16. In addition to the components shown in FIG. 2 and described above, the system of FIG. 4 includes switches 44, 54 and 64 and impedance sensors 40, 50 and 60. Further, the generator 10 also includes a current "on" time calculator 30 and a current "off" time calculator 32 electrically connected to the microprocessor 26. The "on" time calculator 30 determines the amount of the time the current is being supplied to any one of the multiple return electrodes 14, 15 and 16 and transmits this data to the microprocessor 26. Conversely, the "off" time calculator 32 calculates the amount of time that any one of the return electrodes 14, 15 and 16 did not receive any current or the RF output current was turned "off" and sends a signal to the microprocessor 26 via one of its input ports.

The return electrodes 14, 15 and 16 are electrically connected in series to the current monitors 43, 53 and 63 and the switches 44, 54 and 64, respectively. The current monitors 43, 53 and 63 are connected to the microprocessor 26 and report the current passing through the respective return electrodes 14, 15 and 16. The switches 44, 54 and 64 are connected to the time calculators 30 and 32 so that the time calculators 30 and 32 can calculate if the return electrodes 14, 15 and 16 are included in the circuit. In addition, the switches 44, 54 and 64 are connected to a controller 25 which regulates whether the switches 44, 54 and 64 are open or closed.

The return electrodes 14, 15 and 16 include a pair of split pads 41, 42, 51, 52, 61 and 62, respectively, which are electrically connected to impedance sensors 40, 50 and 60. The function of the sensors 40, 50 and 60 will be discussed with reference only to the sensor 40 and its corresponding components. The sensor 40 measures the impedance between the split pads 41, 42 of the return electrode 14 to determine the degree of adherence of the return electrode 14. That is, if a portion of the return electrode 14 becomes detached from the patient, the impedance will increase. The sensor 40 transmits a signal indicative of the measured impedance to an input port of the microprocessor 26. Those skilled in the art will appreciate that the return electrodes 14, 15 and 16 may include multiple pairs of split pads.

In using multiple return electrodes, monitoring the total current output by the generator 10 is an inaccurate measure of the current passing through each of the return electrodes 14, 15 and 16. Therefore, the system according to the present disclosure places the current monitors 43, 53 and 63 and the switches 44, 54 and 64 in series with the corresponding return electrodes 14, 15 and 16. The switches 44, 54 and 64 can be active components, such as transistors of various types, (e.g., field effect transistor, insulated gate bipolar transistor, etc.) or electromechanical components (e.g., relays, solenoid switches, etc.).

The return electrodes 14, 15 and 16 are connected to the generator 10 through the cable 12. As will be discussed in more detail below, to obtain current measurements for each of the individual return electrodes 14, 15 and 16, the current monitors 43, 53 and 63 are included in the circuit between the return electrodes 14, 15 and 16 and the cable 12. The switches 44, 54 and 64 are also incorporated into the circuit in the same manner.

Figure 5:
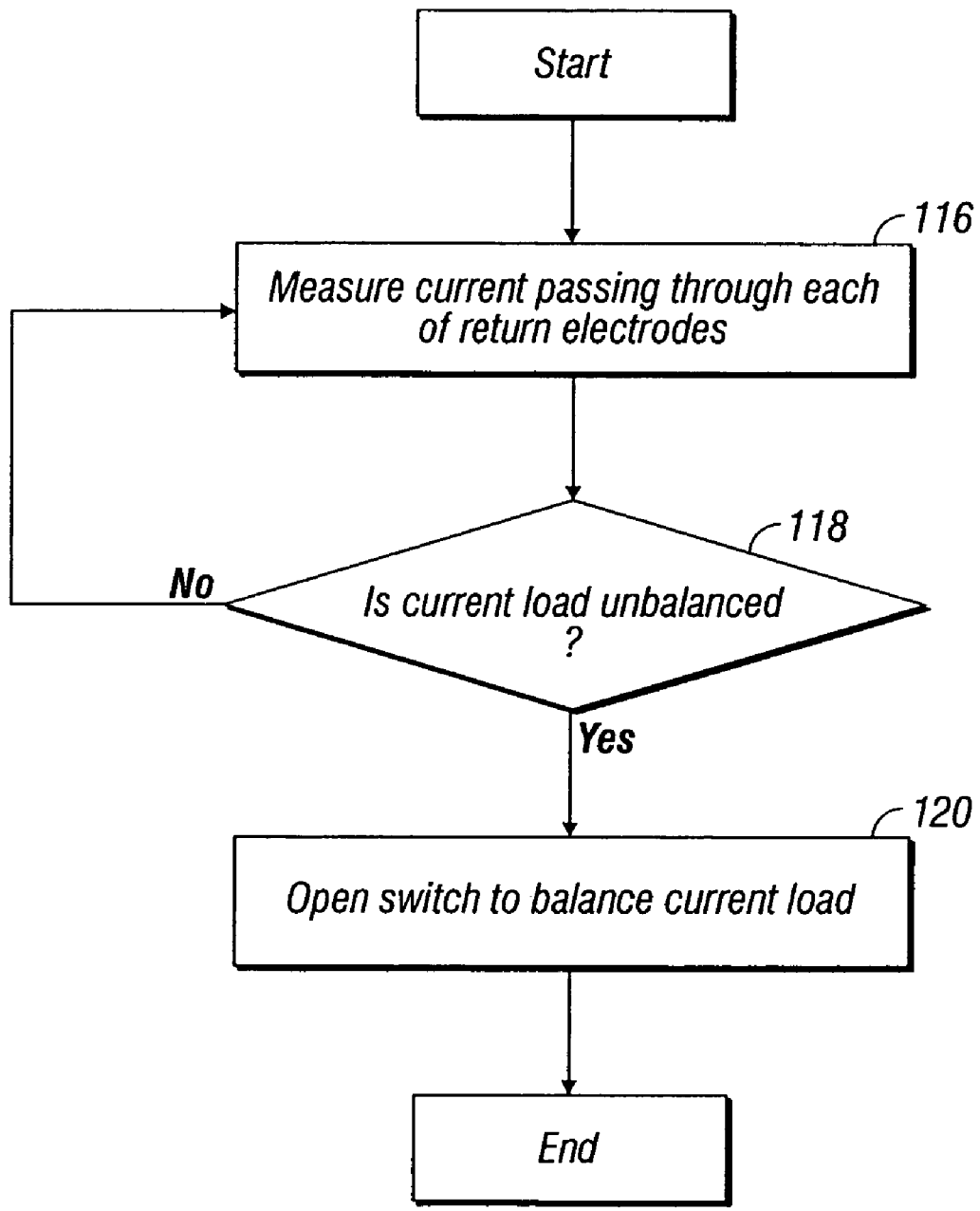
FIG. 5 is a flow diagram showing a method for monitoring and controlling return electrode current in multiple return electrodes.

Monitoring and controlling of current passing through the return electrodes 14, 15 and 16 for balancing thermal effects will be discussed in conjunction with FIG. 5. In step 116, the current passing through each of the return electrodes 14, 15 and 16 is measured using the respective current monitors 43, 53 and 63 (Imx, wherein x is the number of the current monitor) and is transmitted to the microprocessor 26. The microprocessor 26 sends the measurements to the comparator 34.

In step 118, the comparator 34 determines if the current load is unbalanced, for instance, the current passing through the return electrode 14, is higher than the current passing through other return electrodes 15 and 16. This determination is made by initially calculating total current (Itotal), which is the sum of current measured for each of the return electrodes 14, 15 and 16. Additionally, an average current value (Iavg) is calculated by dividing the total amount of current (Itotal) by the number of return electrodes.

If the current passing through the return electrode 14 is higher than the calculated average current value, then it is expected that the return electrode 14 will overheat and possibly damage tissue. Therefore, in step 120, the comparator 34 notifies the controller 25 of the imbalance in the current of the return electrode 14. The controller 25 then opens the switch 44 for a predetermined off-time period (Toff) to distribute the current load more evenly through the other return electrodes 15 and 16. This balances the current load and the thermal load across all of the return electrodes 14, 15 and 16.

The off-time period (Toff) is determined based on a desired maximum off-time period (Toffmax), predetermined minimum off-time period (Toffmin), total current value (Itotal) and maximum current value (Imax). The maximum current value (Imax) is the maximum allowable current which is set based on the desired current balancing requirements. The maximum current value (Imax) can be defined as a sum of the current average (Iavg) and an acceptable tolerance, wherein the tolerance can be from about 0 mA to about 100 mA. Further, tolerance can also be a percentage of the average current value from about 0% to about 25%. The maximum off-time period (Toffmax) and minimum off-time period (Toffmin) are the maximum and minimum time periods, respectively, representing a time period during which a return electrode can be removed from the circuit. The off-time period (Toff) is calculated using the following formula:

$$Toff=(Toffmax-Toffmin)/(Itotal-Imax)*Imx$$

Thus, off-time period is expressed as a function of the difference of the maximum and minim off-time periods multiplied by the ratio of the measured current and the difference between the total current and the maximum current. The off-time period (Toff) and maximum current value (Imax) may be adjusted for each individual return electrode.

Switch 44 may be opened using pulse width modulation, which allows for using predetermined pulses to manipulate specific switches. More specifically, a pulsed electrical control signal (e.g., from the microprocessor 26) is used to toggle the switch 44 depending on the duty cycle of the control signal, such as when the signal is "on," the switch 44 is open and when the signal is "off" the switch 44 is closed.

Additional improvements to this algorithm include a comparison of total current (Itotal) to the current (Imain) measured by the output current sensor 28 to determine if there is any unintended leakage paths. The comparison is made by taking into consideration leakage current which can be from about 0 mA to about 150 mA (e.g., IEC 60601-2-2 maximum leakage standard). If total current (Itotal) is larger than main current (Imain) by the corresponding leakage current amount then a warning is given to the user or a control signal issued by the microprocessor 26 to adjust the RF energy supply accordingly.

Those skilled in the art will appreciate that the redistribution of the current load may be accomplished in other ways. For instance, instead of the switch 44, a device that adjusts impedance of the circuit (e.g., resistor network, variable capacitor, transformer coupled load, transistor in linear region, etc.) including the current monitor 42 and the return electrode 14 may be utilized. If an imbalanced current is detected, then the impedance altering device which would be connected in series with the circuit, may raise the impedance and thereby reduce the current passing therethrough.

The current load determining algorithm may be also configured to measure impedance of the return electrodes 14, 15 and 16 and control the current flowing therethrough as a function of the measured impedance. If the return electrode is improperly adhered, the return electrode is going to have increased relative impedance as compared with other return electrodes. As a result, the current passing through the improperly adhered return electrode will decrease. The current monitors 43, 53 and 63 are used to detect the decrease in current and determine if the return electrode having a lower current also corresponds to having an increased impedance thereby confirming that the particular return electrode is improperly adhered and/or positioned.

In a further embodiment of the present disclosure, a system and method are provided for determining the absolute value of the thermal effect of the return electrodes 14, 15 and 16. The value of the thermal effect is determined by measuring the probability of tissue damage using the impedance values at the return electrodes 14, 15 and 16.

An algorithm in the microprocessor 26, described in more detail below, processes the signals from the output current sensor 28, the current monitors 43, 53 and 63 and the time calculators 30 and 32 in the calculation of the probability of tissue damage. The output port of the microprocessor 26 is in electrical communication with the comparator 34. The calculation of microprocessor 26 is compared to threshold values stored in the comparator 34, and if these values are exceeded, a signal is sent to generate an alarm using an alarm 27 as a warning to the user. If the threshold values are exceeded, the comparator 34 also sends a power adjustment signal to the controller 25 which signals the power supply 22 to either adjust, e.g., reduce the RF output current, shut off the power supply 22, or open any of the switches 44, 54 and 64 to terminate the supply of current, depending on the amount that the threshold is exceeded.

The following description is of the formulas and calculations involved in a method to calculate the probability of tissue damage occurring under the return electrodes 14, the same method can be used for the other return electrodes. As previously stated, if the total current passing through the return electrode 14 is increased or the current duty cycle, defined by the percentage of time the generator 10 is "on" during which the current is applied, is increased, heating under the electrode will also increase.

Tissue damage may result when a heating factor of the tissue underneath the return electrode 14 is higher than acceptable. The heating factor of the tissue is a measure of how much heat is dissipated in the tissue. The following formula provides the heating factor (it should be noted that in the formulas described in the disclosure, x represents the number of the associated electrode):

$$\text{Heating Factor}=I_{mx}^2 t_{onx}$$

where $I_{mx}^2$ equals the square of the current in milliamps passing through a return electrode, e.g., $I_{m14}$ is the current passing through the return electrode 14, and $t_{onx}$ equals the time that current is passing through a return electrode, e.g., $t_{on14}$ time on for the return electrode 14. The ($I_{m14}$) is obtained from the corresponding current monitor 43 as discussed in more detail below.

Thus, the heating factor can be defined as the square of a given current passed through the return electrode attached to a patient multiplied by the time the current is applied. As is apparent from the formula, if either the current is increased or the on time is increased, the amount of heat dissipated in the tissue, and thus the chances of tissue damage, are increased.

The foregoing heat factor formula assumes that the area attached to the patient is unchanged. However, as a practical matter, that area can change as a portion of the return electrode can become detached from the patient. The return electrodes 14, 15 and 16 are split to enable the impedance to be measured between two split pads 41 & 42, 51 & 52 and 61 & 62, respectively. The impedance measurement provides an indication of how well the return electrodes 14, 15 and 16 are adhered to the patient since there is a direct relationship between the impedance and the area of patient contact. If the electrode is partially peeled from the patient, the impedance increases. This is because each portion of the electrode pad that touches the patient has a specific resistance. All of these resistances are connected in a parallel circuit, and the resultant equivalent resistance is smaller than any of its individual elements. Therefore, if any of these parallel resistances are removed because of peeling, the equivalent resistance increases slightly.

To accommodate for changed surface contact area of the return electrode, a constant ($K_{hx}$) is added to the formula where $K_{hx} \geq 1$. For example, $K_{h14}=1$ when the return electrode 14 is fully adhered, and $K_{hx}>1$ if the return electrode 14 is not fully adhered. The following formula represents the modification:

$$\text{Heating Factor} = K_{hx} I_{mx}^2 t_{onx}$$

As is apparent from the formula, if the surface contact area of the return electrode 14 decreases, since ($K_{h14}$) will be greater than 1, the heating factor will increase. As the surface area decreases, as explained above, the current density increases and the amount of heating for a given output current also increases. It is to be appreciated the range of values of constant K can be determined from empirical data and stored as a database, chart, etc, which can be accessed using the measured impedance value.

Another factor affecting dissipation of heat in the tissue is the time period the RF energy is applied. The patient's body has the ability to remove heat from the area under the return electrode by the blood flow in the capillaries, small arteries and small veins. The more time between the applications of RF energy, the greater the heat removal because the body will have more time to naturally remove the heat. This ability to remove heat over a period of time can be represented by the following formula:

$$\text{Cooling factor} = K_{cx} t_{offx}$$

where ($K_{c14}$) is a cooling constant for the return electrode 14 dependent on the patient and ($t_{off14}$) is the time in seconds that current is not passing through the return electrode 14.

Figure 6:
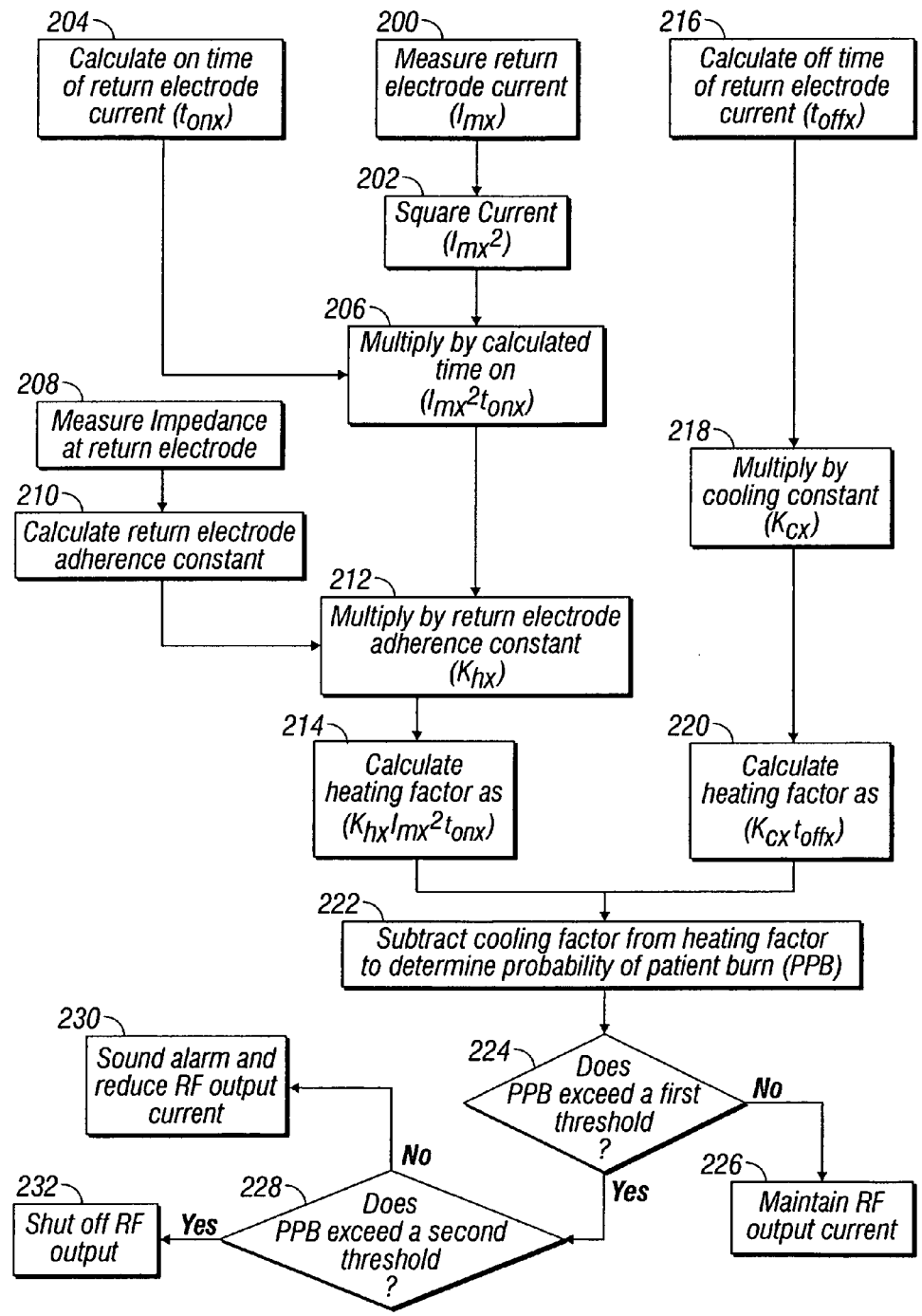
FIG. 6 is a flow diagram showing a method for determining the probability of tissue damage.

The above-described formulas allow the method and system of the present disclosure to measure the current delivered and the time period the current is delivered, as well as calculate and compare the heating and cooling factors to measure the probability of tissue damage as shown in FIG. 6. The method shown in FIG. 6 will be discussed with reference to the return electrode 14 and its corresponding components.

In step 200, the current passing through the return electrode 14 ($I_{m14}$) is measured by the current monitor 43. In step 202, the current monitor 43 transmits the measurement to the microprocessor 26 which squares the measurement, represented by ($I_{m14}^2$) in milliamps. In step 204, the time that the current being applied through the return electrode 14 ($t_{on14}$) is measured in seconds. The ($t_{on14}$) for the return electrode 14 is defined as the time during which the generator 10 is activated and the return electrode 14 is in the circuit, e.g., the switch 44 is closed. The ($t_{on14}$) is calculated by the time calculator 30 based on the readings from the output current sensor 28 and the switch 44. In step 206, the microprocessor 26 multiplies the time on ($t_{on14}$) by the squared current ($I_{m14}^2$), the formula being represented by ($I_{m14}^2$)*($t_{on14}$) to yield a first value.

In step 208, the impedance sensor 40 measures the impedance at the return electrode 14 which is indicative of the degree of adherence of the return electrode 14 to the patient. In step, 210 the adherence constant ($K_{h14}$) is calculated. In step 212, the microprocessor 26 multiplies the adherence constant ($K_{h14}$) by ($I_{m14}^2$)*($t_{on14}$) to calculate the heating factor in step 214. Thus, the heating factor is calculated by the algorithm which multiplies ($K_{h14}$) by ($I_{m14}^2$)*($t_{on14}$) wherein ($K_{h14}$) is the adherence constant and K=1 when the return electrode is fully adhered to the patient and K>1 if the electrode is not fully adhered.

The cooling factor is calculated by the measured time the current is not being applied. More specifically, in step 216, the time "off" for the return electrode 14 in seconds of the output current ($t_{off14}$) is calculated. The ($t_{off14}$) for the return electrode 14 is defined as time during which the generator 10 is deactivated or when the return electrode 14 is not in the circuit, e.g., the switch 44 is open. The ($t_{off14}$) is calculated by the time calculator 32 based on the readings from the output current sensor 28 and the switch 44. In step 218, the microprocessor 26 multiplies the time off ($t_{off14}$) by the cooling constant ($K_{c14}$) to calculate the cooling factor as ($K_{c14}$)*($t_{off14}$) in step 220. The cooling constant ($K_{c14}$) takes into account the patient body's natural cooling where the blood flow in the capillaries, small arteries and veins of the patient cools the tissue over time. For example, assuming tissue normally cools at one degree per minute, since there is some variation, the cooling constant could be conservatively selected as ½ degree per minute. Other constants could be selected depending on the tissue cooling time.

In step 222, the cooling factor is subtracted from the heating factor by the microprocessor 26 to determine a difference value representative of the probability of tissue damage. In step 224, the microprocessor 26 sends a signal to the comparator 34 representative of the difference value and the comparator 34 compares the difference value to a first threshold value. If the difference value is less than or equal to the first threshold value, a signal sent to the controller 25 and to the power supply 22 maintains the RF output current in step 226. This indicates that the differential between the cooling factor and heating factor is relatively low, hence there is a low probability of tissue damage and no adjustments to the current passing through the return electrode 14 need to be made.

If the difference value exceeds the first threshold value, in step 228, the difference value is then compared by the comparator 34 to a second threshold predetermined value in step 228. The second threshold value is preset to correspond to the situation where tissue damage is highly likely and the RF current through the tissue needs to be terminated. If the difference value exceeds the second threshold value, this indicates that the heating factor is too high relative to the cooling factor. In step 232, the comparator 34 will transmit a second signal to the controller 25. The controller 25 will process this signal and generate a shut off signal to the power supply 22 to shut off the RF current or to the switch 44 to turn off the current passing only through the return electrode 14. This shut off will allow the body time to dissipate the heat and cool the tissue.

Both threshold values are predetermined based on the probability of tissue damage so the overheating of tissue can be timely detected and the electrosurgical generator adjusted accordingly. If the difference value exceeds the first threshold value, but does not exceed the second threshold value, this means that although the heating factor is relatively high and there is some probability of tissue damage at the present power levels, it is not high enough that a shut down is mandated. Instead, the output level needs to be reduced. In this circumstance, in step 230, the comparator 34 will transmit a third signal to the controller 25 indicative of the high probability of tissue damage. The controller 25, in turn, will transmit a signal to the power supply 22 or to the switch 44 to reduce the output power to thereby reduce the output current by a preset amount.

It is also contemplated that if the difference value falls between the first threshold value and the second threshold value, rather than reducing the power, the duty cycle can be reduced. The duty cycle reduction could also alternately be the first response if the probability of tissue damage exceeds a first threshold followed by a reduction in power if the first threshold is further exceeded.

Thus, the system 1 remains operational, but at reduced current levels, to reduce the heating effect on the tissue. The probability of tissue damage is preferably continuously calculated in this manner throughout the surgical procedure to continuously monitor and control the heating of tissue.

As indicated in FIGS. 2 and 4, if the probability of tissue damage exceeds the first threshold value an alarm signal is sent to the alarm 27 to generate an alarm. The alarm can be in the form of a visual indicator, an audible indicator or both. Additionally, a visual and/or audible alarm can be sounded if the probability of tissue damage exceeds the second threshold value indicating shut off of the power supply.

In an alternate embodiment, the system and method according to the present disclosure include an additional step of determining the size of the return electrode to be utilized, e.g. adult, infant, neonate, and adjusting the heating and cooling constants accordingly. The user could inform the generator of the size being used, or alternatively, the size can be automatically sensed by the generator based on the differences in the return electrode connector.

The system and method according to the present disclosure monitors the current, calculates the probability of tissue damage for each of the multiple return electrodes, and adjusts the current passing through the multiple return electrodes accordingly. Since conventional return electrodes are connected in parallel, it is very difficult to calculate those values using the total current output. The system according to the present disclosure overcomes this difficulty by using individual current monitors and impedance sensors for each of the multiple return electrodes. These devices report the current and the impedance values of each of the return electrode circuits. Using current values as part of the heating factor calculation is believed to increase the accuracy of the probability of a tissue damage determination since current values are believed to actually cause the heating of the tissue. These values allow the electrosurgical system to prevent tissue damage by diverting current or completely turning current off and balancing the thermal effect over multiple return electrodes. This feature, in turn, allows for more energy to be applied during the procedure as a whole as well as increases the length of the surgical procedure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A system for monitoring a plurality of return electrodes, the system comprising:

an electrosurgical generator adapted to generate an electrosurgical current and an interrogatory low current pulse;

a plurality of return electrodes adhered to a patient and adapted to couple to the electrosurgical generator;

a current monitor connected in series with each of the plurality of the return electrodes to measure a current signal passing therethrough;

a processor coupled to each of the current monitors, the processor configured to determine prior to application of the electrosurgical current a desired current ratio based on the interrogatory low current pulse and an actual current ratio for each of the plurality of the return electrodes as a function of the electrosurgical current passing through each of the plurality of the return electrodes, the processor further configured to compare the desired current ratio and the actual current ratio.

2. A system according to claim 1, wherein the processor determines the actual current ratio as a function of the interrogatory tow current pulse passing through each of the plurality of the return electrodes.

3. A system according to claim 1, wherein the processor determines the actual current ratio as a function of the electrosurgical current passing through each of the plurality of the return electrodes.

4. A system according to claim 1, wherein the processor compares the desired current ratio and the actual current ratio to determine if each of the plurality of the return electrodes is at least one of properly positioned and properly adhered.

5. A system according to claim 4, wherein the processor outputs a notification signal if the actual current ratio differs from the desired current ratio by a predetermined threshold, wherein the notification signal alerts a user to check at least one of position and adherence of each of the plurality of the return electrodes.

6. A system according to claim 4, wherein the processor signals the electrosurgical generator to adjust output of the electrosurgical current if the actual current ratio differs from the desired current ratio by a predetermined threshold.

7. A method for monitoring a plurality of return electrodes, the method comprising:

providing a plurality of return electrodes adhered to a patient and coupled to an electrosurgical generator configured to generate an electrosurgical current and a current monitor connected in series with each of the plurality of the return electrodes;

generating an interrogatory low current pulse prior to generating the electrosurgical current;

determining a desired current ratio for each of the plurality of the return electrodes prior to application of the electrosurgical current based on the interrogatory low current pulse;

measuring a current passing through each of the plurality of the return electrodes;

determining an actual current ratio as a function of the current passing through each of the plurality of the return electrodes; and comparing the desired current ratio and the actual current ratio.

8. A method according to claim 7, further comprising the step of:

determining the actual current ratio as a function of the interrogatory low current pulse passing through each of the plurality of the return electrodes.

9. A method according to claim 7, further comprising the step of:

determining the actual current ratio as a function of the electrosurgical current passing through each of the plurality of the return electrodes.

10. A method according to claim 7, further comprising the step of:

comparing the desired current ratio and the actual current ratio to determine if each of the plurality of the return electrodes is at least one of properly positioned and properly adhered.

11. A method according to claim 10, further comprising the step of outputting a notification signal if the actual current ratio differs from the desired current ratio by a predetermined threshold, wherein the notification signal alerts a user to check at least one of the position and adherence of each of the plurality of the return electrodes.

12. A method according to claim 10, further comprising the step of:

signaling the electrosurgical generator to adjust output of the electrosurgical current if the actual current ratio differs from the desired current ratio by a predetermined threshold.

* * * * *